United States Patent
Ueda et al.

(10) Patent No.: US 8,279,443 B2
(45) Date of Patent: Oct. 2, 2012

(54) BIOINSTRUMENTATION APPARATUS

(75) Inventors: Yukio Ueda, Hamamatsu (JP); Yutaka Yamashita, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 204 days.

(21) Appl. No.: 12/672,203

(22) PCT Filed: Oct. 10, 2008

(86) PCT No.: PCT/JP2008/068485
§ 371 (c)(1),
(2), (4) Date: Feb. 4, 2010

(87) PCT Pub. No.: WO2009/054278
PCT Pub. Date: Apr. 30, 2009

(65) Prior Publication Data
US 2011/0063624 A1    Mar. 17, 2011

(30) Foreign Application Priority Data
Oct. 24, 2007    (JP) .............................. P2007-276770

(51) Int. Cl.
*G01N 21/00* (2006.01)
*A61B 5/05* (2006.01)

(52) U.S. Cl. ......... 356/432; 600/425; 600/407; 600/310

(58) Field of Classification Search .......... 356/432–440; 600/425, 407, 310, 322, 473, 476; 382/131
See application file for complete search history.

(56) References Cited

U.S. PATENT DOCUMENTS

| | | | |
|---|---|---|---|
| 5,983,121 A * | 11/1999 | Tsuchiya | 600/310 |
| 7,809,431 B2 * | 10/2010 | Texier-Nogues et al. | 600/476 |
| 2002/0099287 A1 * | 7/2002 | Ohmae et al. | 600/425 |
| 2010/0256496 A1 * | 10/2010 | Zhu | 600/459 |

FOREIGN PATENT DOCUMENTS

| | | |
|---|---|---|
| JP | 10-500338 | 1/1998 |
| JP | 10-073481 | 3/1998 |
| JP | 11-173976 | 7/1999 |
| JP | 2000-146828 | 5/2000 |
| JP | 3771364 | 2/2006 |

* cited by examiner

*Primary Examiner* — Hoa Pham
(74) *Attorney, Agent, or Firm* — Drinker Biddle & Reath LLP

(57) ABSTRACT

A bioinstrumentation apparatus irradiates light onto a measured region of a subject, detects diffused light to acquire internal information on the measured region, and includes: a container holding a light transmitting medium; a light irradiation unit including a plurality of light emitting ends fixed to the container and irradiating a first light and a second light that mutually differ in wavelength onto the measured region that is immersed in the medium; a light detection unit including a plurality of light detecting ends fixed to the container and detecting the diffused light from the measured region; and a computing unit computing the internal information based on an output signal from the light detection unit; the wavelength of the first light being a wavelength at which an absorption coefficient of the measured region and a mean value of absorption coefficient of the medium are substantially equal, the wavelength of the second light being a wavelength at which the absorption coefficient of the measured region is greater than the mean value of the absorption coefficient of the medium, and the computing unit computing the internal information based on an output signal related to diffused light of the first light and computing boundary information between the measured region and the medium based on an output signal related to diffused light of the second light.

4 Claims, 11 Drawing Sheets

BIOINSTRUMENTATION APPARATUS

TECHNICAL FIELD

The present invention relates to a bioinstrumentation apparatus.

BACKGROUND ART

As an apparatus for non-invasively measuring internal information of a living object, such as a head or breast, an apparatus that makes use of light absorbing characteristics of the living object to acquire the internal information has been proposed (refer, for example, to Patent Document 1). With such a measuring apparatus, light is irradiated from a predetermined irradiation position to a region of a living object to be measured, light that is propagated while being scattered in an interior of the measured region is detected at a predetermined detection position, and from a measurement result of an intensity, time waveform, etc., of the detected light, internal information on the measured region, that is, information on a light absorbing body, such as a tumor, etc., present in the interior of the measured region can be acquired.

Also in Patent Document 1, it is described that a medium (hereinafter, referred to as an "optical interface material"), having substantially the same optical characteristics as the measured region at a wavelength of the irradiated light (measurement wavelength), is interposed between the measured region and the light irradiation position and between the measured region and the detection position to prevent reflection, scattering, etc., of light at a surface of the measured region and thereby improve measurement precision.

Patent Document 1: Japanese Published Examined Patent Appliction No. 3771364

DISCLOSURE OF THE INVENTION

Object(s) of the Invention

When the abovementioned optical interface material is interposed between the light irradiation position and the measured region, a relative position of the light absorbing body present in the interior of the measured region with respect to the light irradiation position and the detection position can be measured with good precision because the measured region and the medium have substantially the same optical characteristics at the measurement wavelength. However, it is difficult to distinguish the optical interface material and the measured region, and it is thus difficult to measure a location of the light absorbing body with respect to an entirety of the measured region. It is thus difficult to perform a comparative study with respect to measurement results of an X-ray inspection apparatus, an MRI apparatus, an ultrasonic diagnosis apparatus, or other medical imaging diagnosis apparatus, or to perform biopsy for acquiring a tissue specimen of a tumor.

The present invention has been made in view of the above issue, and an object thereof is to further achieve, in a bioinstrumentation apparatus that irradiates light onto a measured region of a subject and detects diffused light to acquire internal information on the measured region, acquisition of a location of a tumor or other light absorbing body with respect to an entirety of the measured region in addition to the internal information of the measured region.

Means for Solving the Problem

To achieve the above object, a bioinstrumentation apparatus according to the present invention is a bioinstrumentation apparatus that irradiates light onto a measured region of a subject, detects diffused light to acquire internal information on the measured region, and includes: a container holding a light transmitting medium; a light irradiation unit including a plurality of light emitting ends fixed to the container and irradiating a first light and a second light that mutually differ in wavelength onto the measured region that is immersed in the medium; a light detection unit including a plurality of light detecting ends fixed to the container and detecting the diffused light from the measured region; and a computing unit computing the internal information based on an output signal from the light detection unit; the wavelength of the first light being a wavelength at which an absorption coefficient of the measured region and a mean value of absorption coefficient of the medium are substantially equal, the wavelength of the second light being a wavelength at which the absorption coefficient of the measured region is greater than the mean value of the absorption coefficient of the medium, and the computing unit computing the internal information based on an output signal related to diffused light of the first light and computing boundary information between the measured region and the medium based on an output signal related to diffused light of the second light.

With the bioinstrumentation apparatus, two types of measurement, that is, internal information measurement and contour measurement can be performed. With the internal information measurement, the light irradiation unit illuminates the first light onto the measured region immersed in the medium, the diffused light of the first light is detected by the light detection unit, and the computing unit computes the internal information based on the detection result. In the contour measurement, the light irradiation unit illuminates the second light onto the measured region immersed in the medium, the diffused light of the second light is detected by the light detection unit, and the computing unit computes the boundary information between the measured region and the medium (that is, the contour information of the measured region) based on the detection result.

At the wavelength ($\lambda 1$) of the first light, the absorption coefficient ($\mu ab$) of the measured region is practically equal to the absorption coefficient ($\mu ai$) of the medium (that is, $\mu ab(\lambda 1)=\mu ai(\lambda 1)$). Thus, with the internal information measurement using the first light, reflection, scattering, etc., of light at the surface of the measured region is prevented, and a position and size of a tumor or other light absorbing body on the basis of the light irradiation positions and the detection positions can be measured with good precision. Meanwhile, at the wavelength ($\lambda 2$) of the second light, the absorption coefficient ($\mu ab$) of the measured region is greater than the absorption coefficient ($\mu ai$) of the medium (that is, $\mu ab(\lambda 2)>\mu ai(\lambda 2)$). Thus, with the contour measurement using the second light, the contour information of the measured region on the basis of the light irradiation positions and the detection positions can be measured with good precision. By then integrating the internal information measurement result and the contour measurement result, a location of the light absorbing body with respect to an entirety of the measured region can be acquired.

Thus, with the bioinstrumentation apparatus described above, not only the presence/non-presence and size of a tumor or other light absorbing body but the location of the light absorbing body with respect to an entirety of the measured region can be measured with good precision in the apparatus that irradiates light onto the measured region of the subject and detects the diffused light to acquire the internal information on the measured region.

Also, with the bioinstrumentation apparatus, the absorption coefficient of the medium with respect to the first light may be greater than the absorption coefficient of the medium with respect to the second light. In a case where the absorption coefficients $\mu ab(\lambda 1)$ and $\mu ab(\lambda 2)$ of the measured region are equal to each other, the relationships, $\mu ab(\lambda 1) = \mu ai(\lambda 1)$ and $\mu ab(\lambda 2) > \mu ai(\lambda 2)$, can be realized favorably by making the absorption coefficients of the medium satisfy: $\mu ai(\lambda 1) > \mu ai(\lambda 2)$. Or, even in a case where the absorption coefficient $\mu ab(\lambda 1)$ of the measured region is greater than $\mu ab(\lambda 2)$, by adjusting the light absorbing characteristics of the medium and setting the wavelengths $\lambda 1$ and $\lambda 2$ so that a difference of the absorption coefficients of the medium $\mu ai(\lambda 1) - \mu ai(\lambda 2)$) is greater than a difference of the absorption coefficients of the measured region $\mu ab(\lambda 1) - \mu ab(\lambda 2)$), the relationships, $\mu ab(\lambda 1) = \mu ai(\lambda 1)$ and $\mu ab(\lambda 2) > \mu ai(\lambda 2)$, can be realized favorably. The internal information measurement and the contour measurement can thus be performed favorably.

Also, with the bioinstrumentation apparatus, the absorption coefficient of the medium with respect to the first light may be made practically equal to the absorption coefficient of the medium with respect to the second light. In a case where the absorption coefficient $\mu ab(\lambda 1)$ of the measured region is less than $\mu ab(\lambda 2)$, the light absorbing characteristics of the medium may be adjusted and the wavelengths $\lambda 1$ and $\lambda 2$ may be set so that the absorption coefficients of the medium are such that $\mu ai(\lambda 1) = \mu ai(\lambda 2)$. The relationships, $\mu ab(\lambda 1) = \mu ai(\lambda 1)$ and $\mu ab(\lambda 2) > \mu ai(\lambda 2)$, can thereby be realized favorably. The internal information measurement and the contour measurement can thus be performed favorably.

Effect(s) of the Invention

By the present invention, a location of a tumor or other light absorbing body with respect to an entirety of a measured region can be measured in addition to internal information of the measured region in a bioinstrumentation apparatus that irradiates light onto the measured region of the subject and detects diffused light to acquire the internal information on the measured region.

DESCRIPTION OF THE SYMBOLS

10 . . . bioinstrumentation apparatus, 12 . . . container, 14 . . . computing/controlling unit, 16 . . . light emitting/detecting end, 18 . . . light shielding plate, 20 . . . optical interface material, 22 . . . light source, 24 . . . optical switch, 26 . . . light source optical fiber, 28 . . . emission optical fiber, 30 . . . photodetector, 32 . . . shutter, 34 . . . detection optical fiber, 36 . . . signal processing circuit, 38 . . . displaying unit, 40a, 40b light source, 42 . . . optical switch, B . . . measured region

BEST MODES FOR CARRYING OUT THE INVENTION

An embodiment of a bioinstrumentation apparatus shall now be described in detail with reference to the attached drawings. In the description of the drawings, elements that are the same shall be provided with the same symbol and redundant description shall be omitted.

Figure 1:
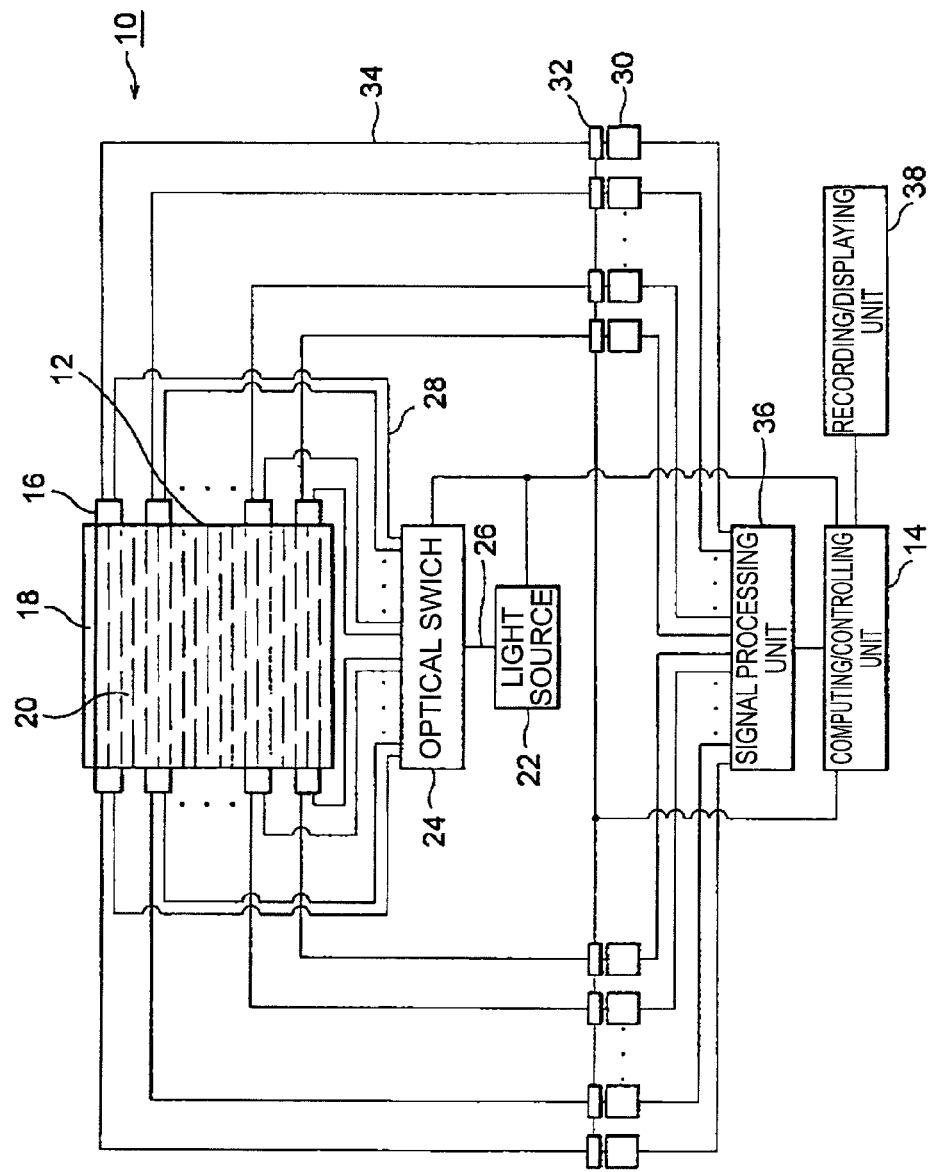
[FIG. 1] is a system arrangement diagram of an embodiment of a bioinstrumentation apparatus.
Figure 2:
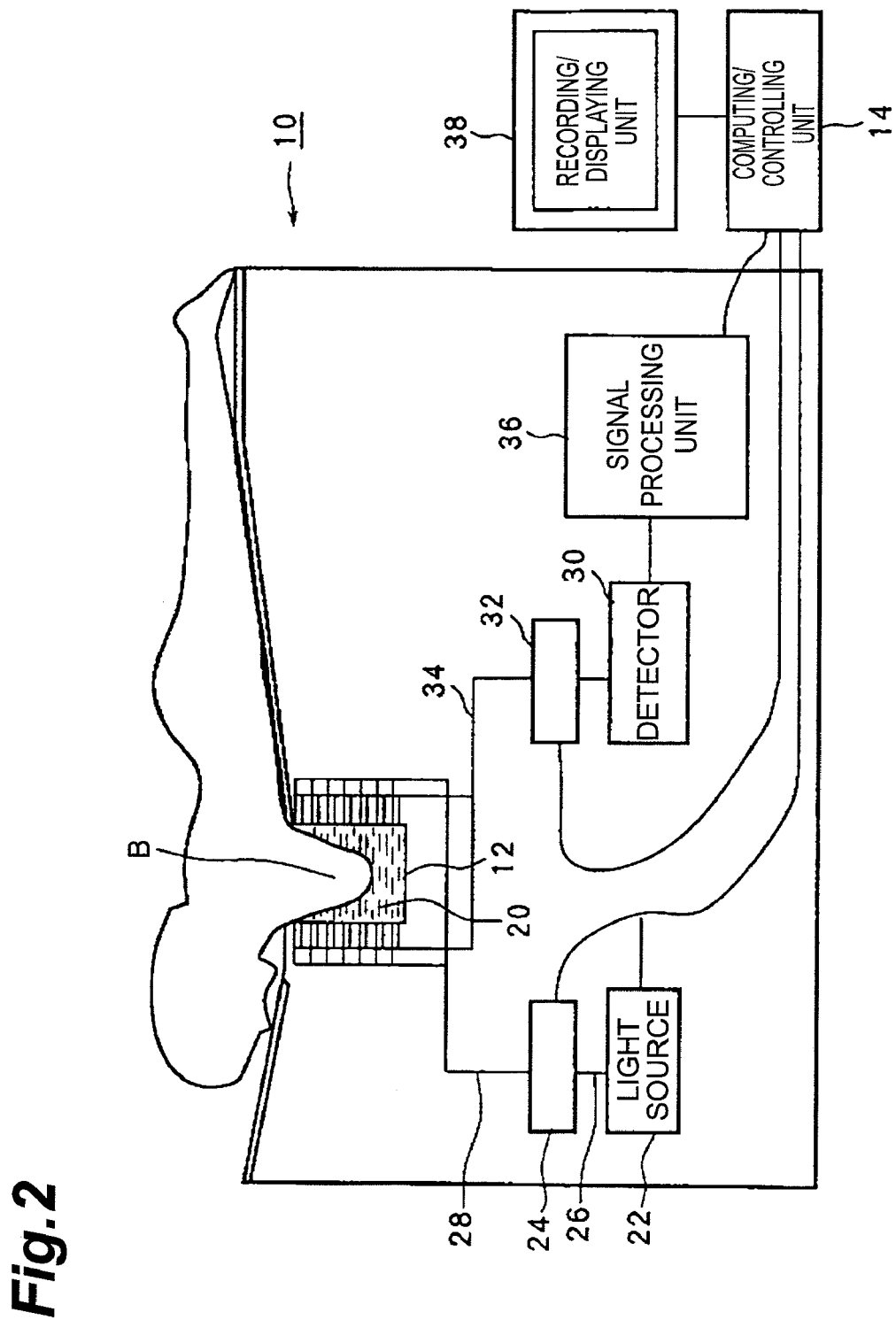
[FIG. 2] is a diagram of a state of use of the bioinstrumentation apparatus shown in FIG. 1.
Figure 3:
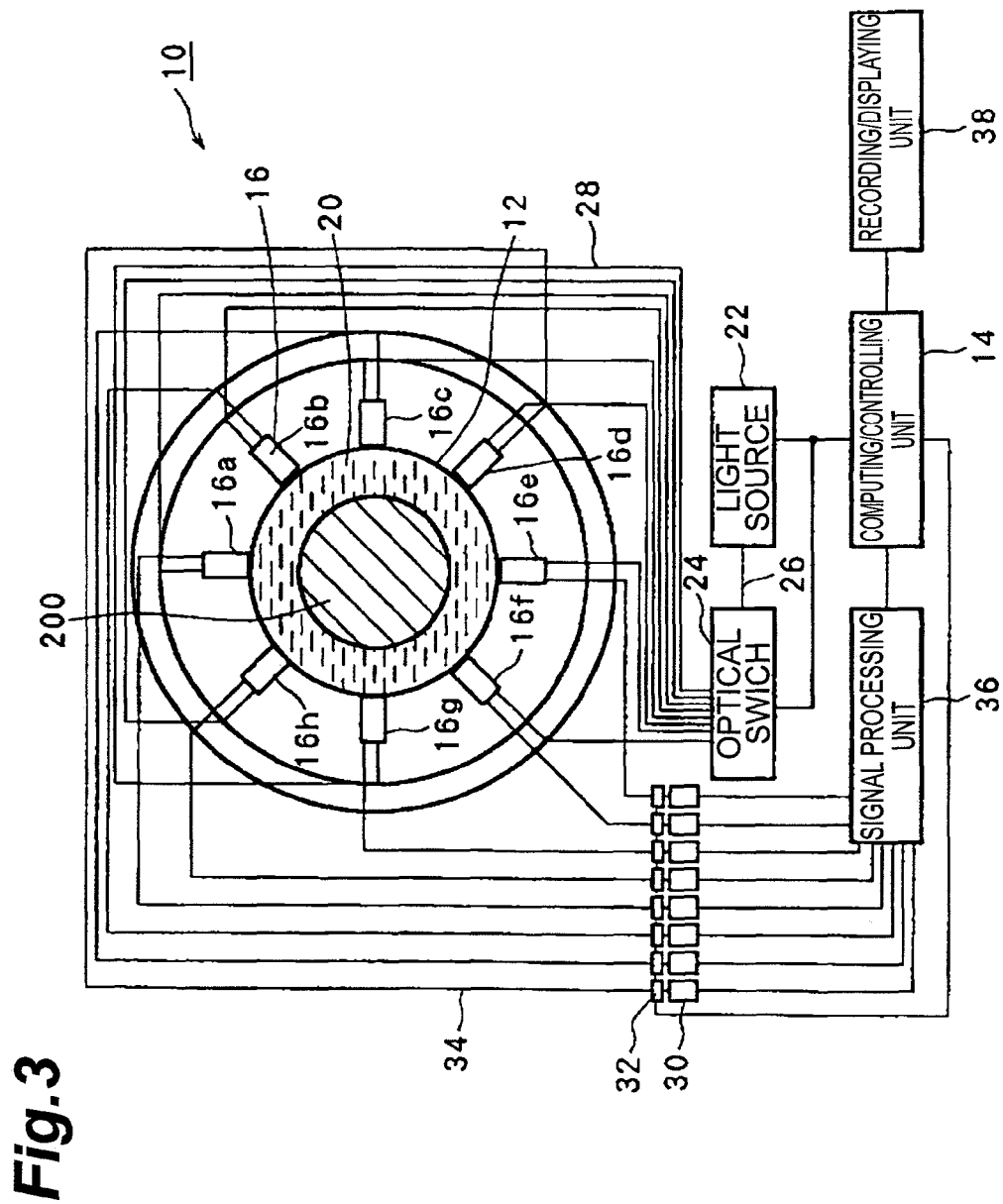
[FIG. 3] is an arrangement diagram of a periphery of a container included in the bioinstrumentation apparatus shown in FIG. 1.

FIG. 1 is a system arrangement diagram of an embodiment of a bioinstrumentation apparatus. FIG. 2 is a diagram of a state of use of the bioinstrumentation apparatus shown in FIG. 1. FIG. 3 is an arrangement diagram of a periphery of a container included in the bioinstrumentation apparatus shown in FIG. 1. The bioinstrumentation apparatus 10 according to the present embodiment irradiates light onto a measured region B of a subject that is a subject of measurement and detects diffused light (returning light) to acquire internal information on (presence/non-presence of a tumor, etc., in) the measured region B. In the present embodiment, a woman's breast is assumed as the measured region B as shown in FIG. 2.

The bioinstrumentation apparatus 10 includes: the container 12, which holds an optical interface material 20 that is a light transmitting medium while the measured region B is introduced thereinto; a light irradiating unit irradiating a first light and a second light that differ mutually in wavelength onto an interior of the container 12; a light detecting unit detecting diffused light arising from the measured region B due to the irradiation of light from the light irradiating unit; and a computing/controlling unit 14 (computing unit) calculating a spatial distribution of an absorption coefficient of the measured region B based on an output signal from the light detecting unit and computing the internal information on the measured region B.

The container 12 has a size enabling the measured region B to be housed adequately and has a cylindrical or semispherical shape with an opening at an upper surface. On an inner surface of the container 12, n (n is an integer no less than 2) light emitting/detecting ends 16 are disposed three-dimensionally at mutually different positions to make up a measuring unit (gantry). Light is emitted successively toward the measured region B from the light emitting ends that the n light emitting/detecting ends 16 have respectively. The light is absorbed and diffused in the measured region B, and the diffused light exiting from the measured region B is made incident on the respective light detecting ends of the n light emitting/detecting ends 16. Although in the present embodiment, n sets of the light emitting/detecting ends 16, each made up of a single set of the light emitting end and the light incident end, are disposed, the light emitting ends and the light detecting ends may be disposed independently at mutually different positions.

The container 12 is made of a light shielding material and prevents light from entering into the interior of the container 12 from besides the light emitting/detecting ends 16. Further, the opening of the container 12 can be covered by a detachable light shielding plate 18. When the light shielding plate 18 is attached to the opening of the container 12, entry of light into the interior of the container 12 from the opening is prevented. Preferably, the inner surface of the container 12 is treated to reduce reflection of the diffused light. For example, the inner surface of the container 12 is formed from an aluminum material that has been subject to anodization (black alumite treatment) and has been colored with a black dye. Or, the inner surface of the container 12 may be formed from a black resin material.

During measurement of a living object, the interior of the container 12 is filled with the optical interface material 20. The optical interface material 20 is a liquid medium that fills gaps between the measured region B and the container 12 to serve a role of reducing discontinuities of optical characteristics at a surface of the measured region B. The optical interface material 20 is arranged so that an absorption coefficient $\mu ai(\lambda 1)$ of the optical interface material 20 at a certain wavelength $\lambda 1$ is practically equal to a mean value $\mu ab(\lambda 1)$ of the absorption coefficient of the measured region B. Further preferably, the optical interface material 20 is arranged so that one or more of its characteristics among the optical characteristics of scattering coefficient, refractive index, optical rotation, polarization degree, etc., are practically equal to a mean value of the scattering coefficient, a mean value of the refractive index, a mean value of the optical rotation, a mean value of the polarization degree, etc., of the measured region B. As an example of the optical interface material 20 in a case where the measured region B is a living object, a solution is used with which the optical characteristics are made close to those of the measured region B by mixing silica or intralipid (fat emulsion), etc., in regard to the scattering coefficient, ink, etc., having a specific absorption coefficient at a specific wavelength, in regard to the absorption coefficient, and glucose or fructose, etc., in regard to the optical rotation and the polarization degree, etc., with water that is substantially equal in refractive index to the living object. Here, "substantially equal" means that a characteristic is equal or can be regarded as being equal from a standpoint of measurement precision, etc.

Figure 4:
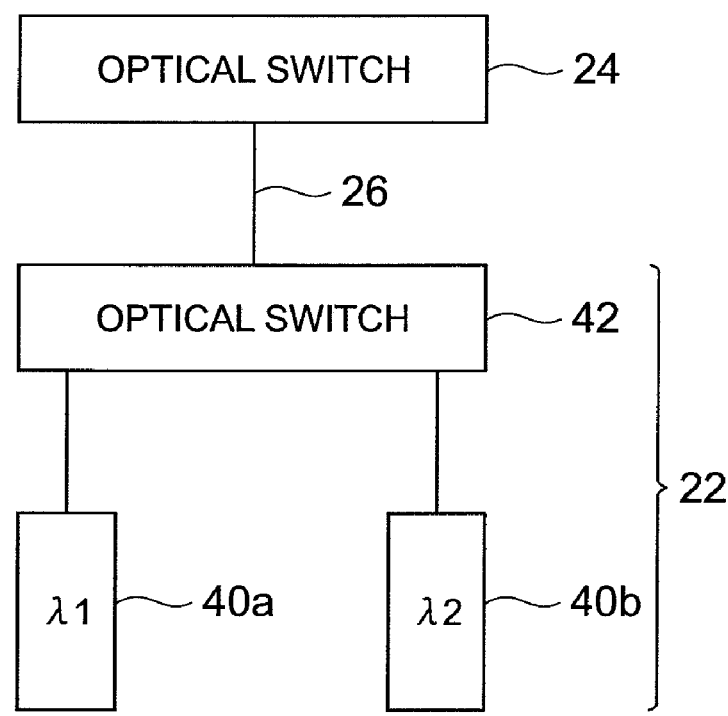
[FIG. 4] is a diagram of an arrangement example of a light source.

A light irradiation unit of the present embodiment is arranged from the light emitting ends that the abovementioned n light emitting/detecting ends 16 have respectively, a light source 22, and an optical switch 24. As the light source 22, for example, a laser diode may be used. The light source 22 in the present embodiment is arranged to be capable of emitting the first light (wavelength: $\lambda 1$) and the second light (wavelength: $\lambda 2$) that differs in wavelength from the first light. As an example of such an arrangement, a variable wavelength laser may be used or the wavelength used may be switched using a wavelength selector, or a light source, having light sources 40a and 40b, respectively generating light of the wavelengths $\lambda 1$ and $\lambda 2$ ($\lambda 1 \neq \lambda 2$), and an optical switch 42 that selects the wavelength by selectively switching between the light sources 40a and 40b as shown in FIG. 4, may be used. Also, as the respective wavelengths $\lambda 1$ and $\lambda 2$ of the first light and second light, wavelengths in a near-infrared region of approximately 700 nm to 900 nm are preferable from a relationship of transmittance of the living object and partial absorption coefficient of the absorbing body to be quantified, etc. Also to reduce measurement time and lighten a burden placed on the subject, the first light and the second light are preferably output with a slight time difference.

Figure 5:
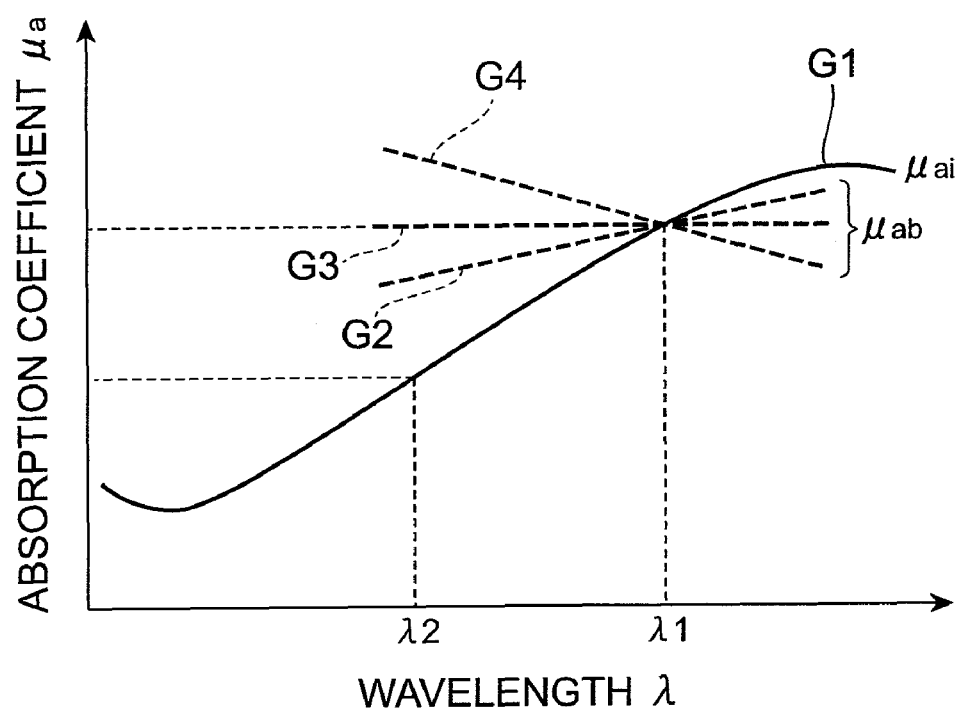
[FIG. 5] is a graph of an example of a relationship of absorption coefficients of an optical interface material and a measured region and a wavelength of light.

Here, FIG. 5 is a graph of an example of a relationship of absorption coefficients $\mu ai$ and $\mu ab$ of the optical interface material 20 and the measured region B and the wavelengths $\lambda 1$ and $\lambda 2$ of light. In FIG. 5, a graph curve G1, indicated by a solid line, shows an example of the relationship of the absorption coefficient $\mu ai$ of the optical interface material 20 and the wavelength of light (a case where the absorption coefficient $\mu ai$ of the optical interface material 20 increases with increase of wavelength). Each of the graph curves G2 to G4, indicated by broken lines, show an example of the relationship of the mean value $\mu ab$ of the absorption coefficient of the measured region B and the wavelength of light (the three cases where the absorption coefficient $\mu ab$ of the measured region B increases, hardly changes, and decreases with increase of wavelength).

As shown in FIG. 5, the wavelength $\lambda 1$ of the first light is set to a wavelength at which the mean value $\mu ab$ of the absorption coefficient of the measured region B is substantially equal to the absorption coefficient $\mu ai$ of the optical interface material (that is, $\mu ab(\lambda 1)=\mu ai(\lambda 1)$). The wavelength $\lambda 2$ of the second light is set to a wavelength at which the mean value $\mu ab$ of the absorption coefficient of the measured region B is greater than the absorption coefficient $\mu ai$ of the optical interface material 20 (that is, $\mu ab(\lambda 2)>\mu ai(\lambda 2)$). In the example shown in FIG. 5, the wavelength $\lambda 2$ is set to a shorter wavelength than the wavelength $\lambda 1$ because a slope of the graph curve G1 is greater than slopes of the graph curves G2 to G4.

FIGS. 1 to 3 are referred to again. The abovementioned first light and the second light are emitted, for example, as continuous lights from the light source 22. The lights emitted from the light source 22 are irradiated from the light emitting/detecting ends 16 onto the measured region B. The optical switch 24 is a 1-input, n-output optical switch that inputs light from the light source 22 via a light source optical fiber 26 and successively supplies the light to each of the above n light emitting/detecting ends 16. That is, with the n emission optical fibers 28 connected to the respective light emitting/detecting ends 16, the optical switch 24 successively selects one optical fiber at a time and optically connects the selected emission optical fiber 28 with the light source 22.

A light detection unit of the present embodiment is made up of the light detecting ends that the n light emitting/detecting ends 16 have respectively, n photodetectors 30 respectively corresponding to the n light emitting/detecting ends 16, and n shutters 32 disposed at front stages of input portions of the respective photodetectors. Into each of the n photodetectors 30, diffused light from the measured region B, made incident on the light detecting end of the corresponding light emitting/detecting end 16, is input via a detection optical fiber 34. The photodetector 30 generates an analog signal according to a light intensity of the diffused light that arrives at the corresponding light emitting/detecting end 16. As the photodetector 30, a photomultiplier tube (PMT) or any of various other photodetectors, such as a photodiode, an avalanche photodiode, a PIN photodiode, etc., may be used. Preferably, the photodetector 30 has spectral sensitivity characteristics enabling adequate detection of wavelength components of the wavelengths $\lambda 1$ and $\lambda 2$. Also, in a case where the diffused light from the measured region B is weak, a photodetector of high sensitivity or high gain is preferably used. A signal processing circuit 36 is connected to a signal output end of the photodetector 30, and the signal processing circuit 36 performs A/D conversion of the analog signal output from the photodetector 30 to generate a digital signal that is in accordance with the light intensity of the diffused light and provides the digital signal to the computing/controlling unit 14.

The computing/controlling unit 14 is a computing unit that performs analysis and computation related to the internal information on the measured region B and boundary information between the measured region B and the optical interface material 20 based on the digital signal provided from the signal processing circuit 36. The computing/controlling unit 14 is realized, for example, by a computer having a computing unit, such as a CPU (Central Processing Unit), and a storage unit, such as a memory, etc. Preferably, the computing/controlling unit 14 further has functions of controlling light emission by the light source 22, operation of the optical switch 24, and opening/closing of the shutter 32. Also, the computing/controlling unit 14 is connected to a recording/displaying unit 38, thereby enabling visualization of the computation results of the computing/controlling unit 14, that is, the internal information on the measured region B and the boundary information between the measured region B and the optical interface material 20.

Computation of the internal information on the measured region B, that is, the internal information measurement is performed, for example, as follows. As shown in FIG. 1, the light shielding plate 18 is fitted onto the container 12 in the state where the interior of the container 12 is filled with the optical interface material 20. The first light (wavelength: λ1) is then successively irradiated onto the interior of the container 12 from each of the n light emitting/detecting ends 16, and light diffused through the optical interface material 20 is detected by the n photodetectors 30 via the n light emitting/detecting ends 16. Apart from this, the measured region B is immersed in the optical interface material 20 in the state where the interior of the container 12 is filled with the optical interface material 20 as shown in FIG. 2. The first light (wavelength: λ1) is then successively irradiated onto the interior of the container 12 from each of the n light emitting/detecting ends 16, and light diffused through the optical interface material 20 is detected by the n photodetectors 30 via the n light emitting/detecting ends 16. By performing, at the computing/controlling unit 14, comparison of the two detection results thus acquired, a spatial distribution of absorption coefficient in the interior of the container 12 is computed to acquire information (internal information) on a position and shape of a tumor or other absorbing body.

Figure 6:
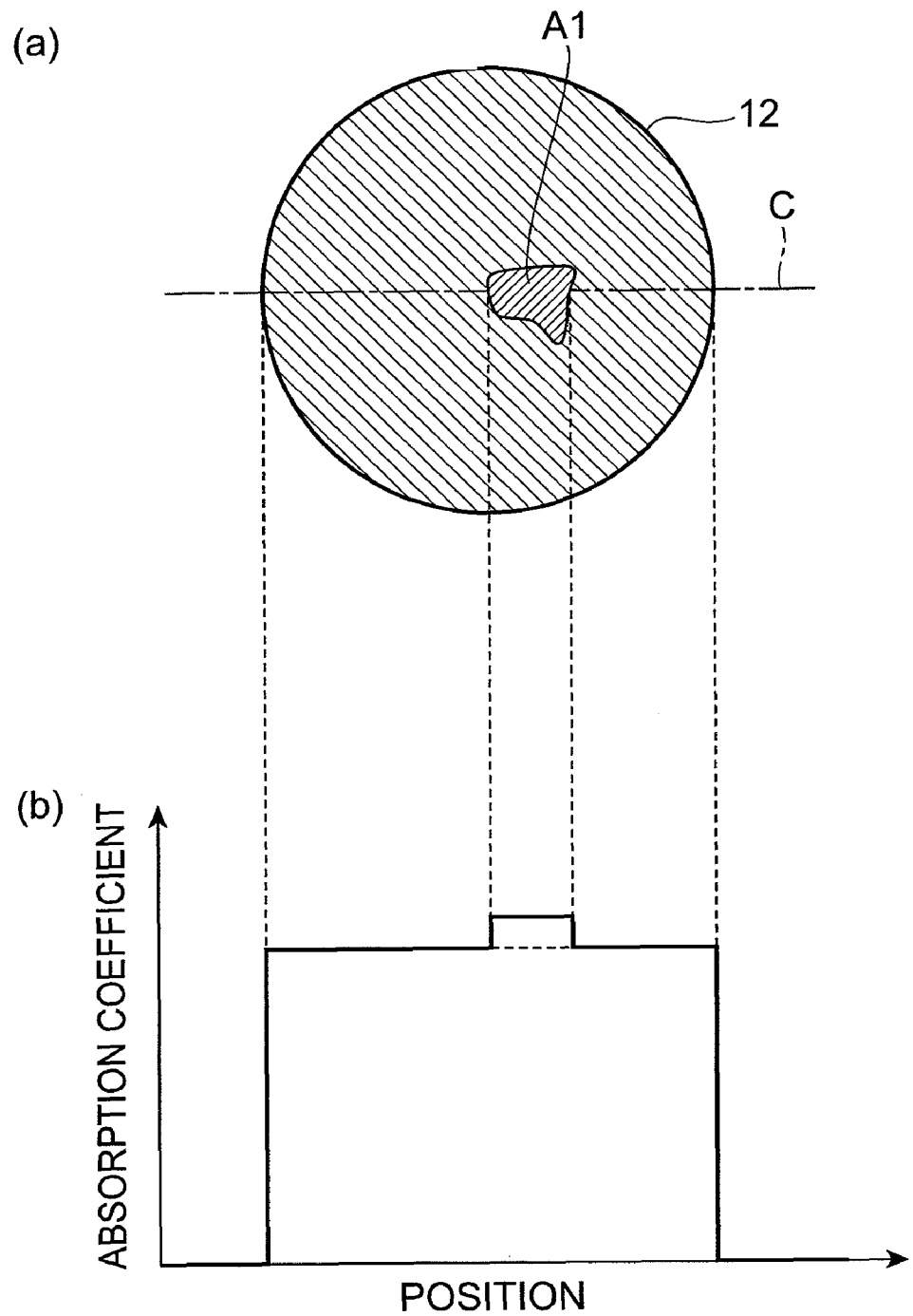
[FIGS. 6A and 6B] are conceptual diagrams of a spatial distribution of absorption coefficient in an interior of the container and show an internal information measurement result.

FIG. 6 shows conceptual diagrams of a spatial distribution of absorption coefficient in the interior of the container 12. In FIG. 6A, a circular frame expresses the container 12. Also, in the inner side of the container 12, a region of higher absorption coefficient is colored darker, and a region A1 of comparatively high absorption coefficient that is present near a center expresses a tumor or other absorbing body present in the interior of the measured region B. In FIG. 6B, an ordinate axis indicates the absorption coefficient and an abscissa axis indicates a position along a hypothetical line C in FIG. 6A. By the above computation, the position, shape, etc., of the region A1 (absorbing body) with respect to the entirety of the container 12 are acquired.

Also, computation of the boundary information between the measured region B and the optical interface material 20, that is, the contour measurement is performed, for example, as follows. As shown in FIG. 2, the measured region B is immersed in the optical interface material 20 in the state where the interior of the container 12 is filled with the optical interface material 20. The second light (wavelength: λ2) is then successively irradiated onto the interior of the container 12 from each of the n light emitting/detecting ends 16, and light diffused through the optical interface material 20 is detected by the n photodetectors 30 via the n light emitting/detecting ends 16. By performing, at the computing/controlling unit 14, comparison of the detection result thus acquired and the detection result acquired in the above-described state where the light shielding plate 18 is fitted onto the container 12, a spatial distribution of the absorption coefficient in the interior of the container 12 is computed to acquire information (contour information) on a position and shape of the measured region B.

Figure 7:
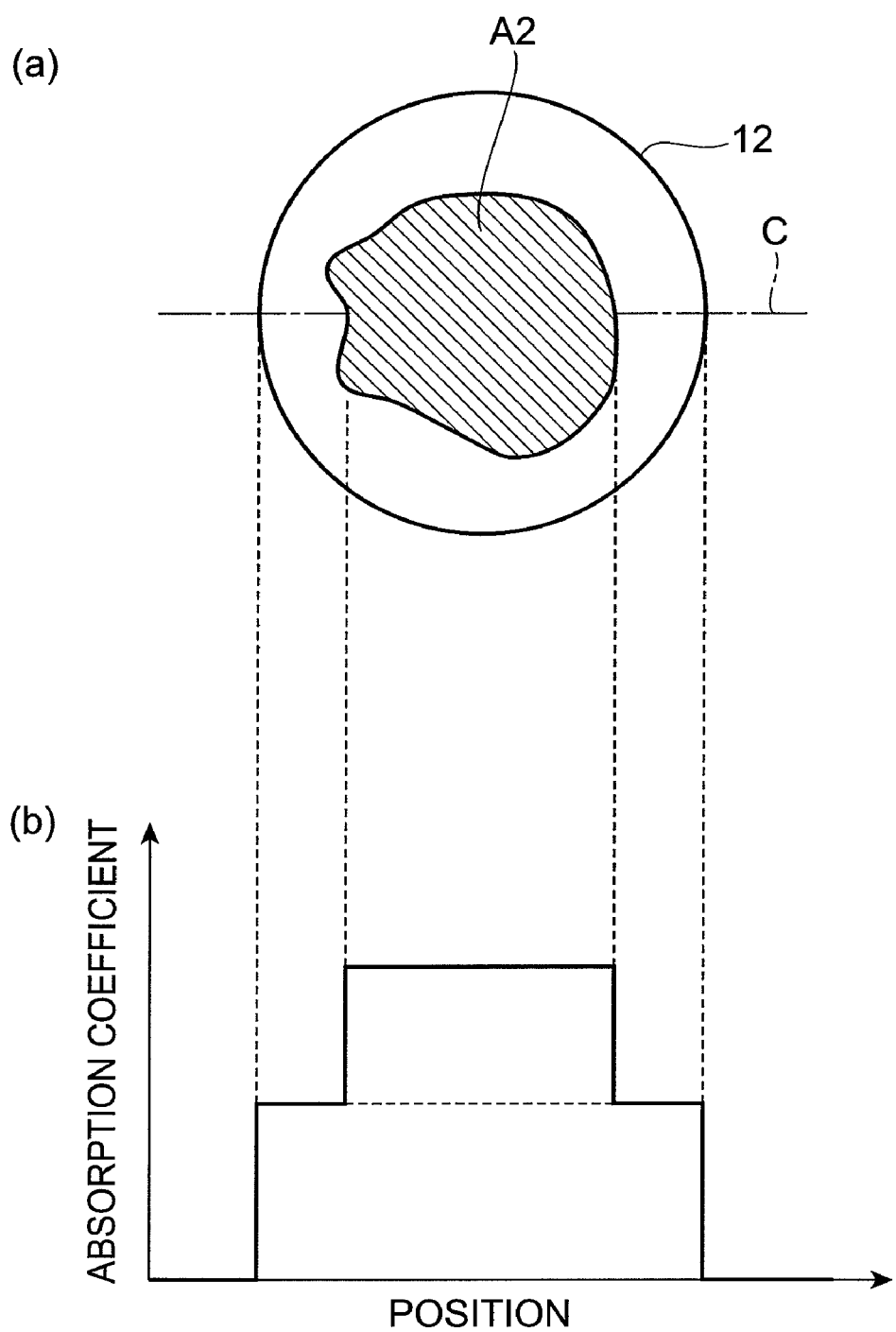
[FIGS. 7A and 7B] are conceptual diagrams of a spatial distribution of absorption coefficient in the interior of the container and show a contour measurement result.

FIG. 7 shows conceptual diagrams of a spatial distribution of absorption coefficient in the interior of the container 12. In FIG. 7A, a region A2 of comparatively high absorption coefficient that is present near the center indicates a region occupied by the measured region B. In FIG. 7B, the ordinate axis indicates the absorption coefficient and the abscissa axis indicates the position along the hypothetical line C in FIG. 7A. By the above computation, the position, shape, etc., of the region A2 (measured region) with respect to the entirety of the container 12 are acquired.

Figure 8:
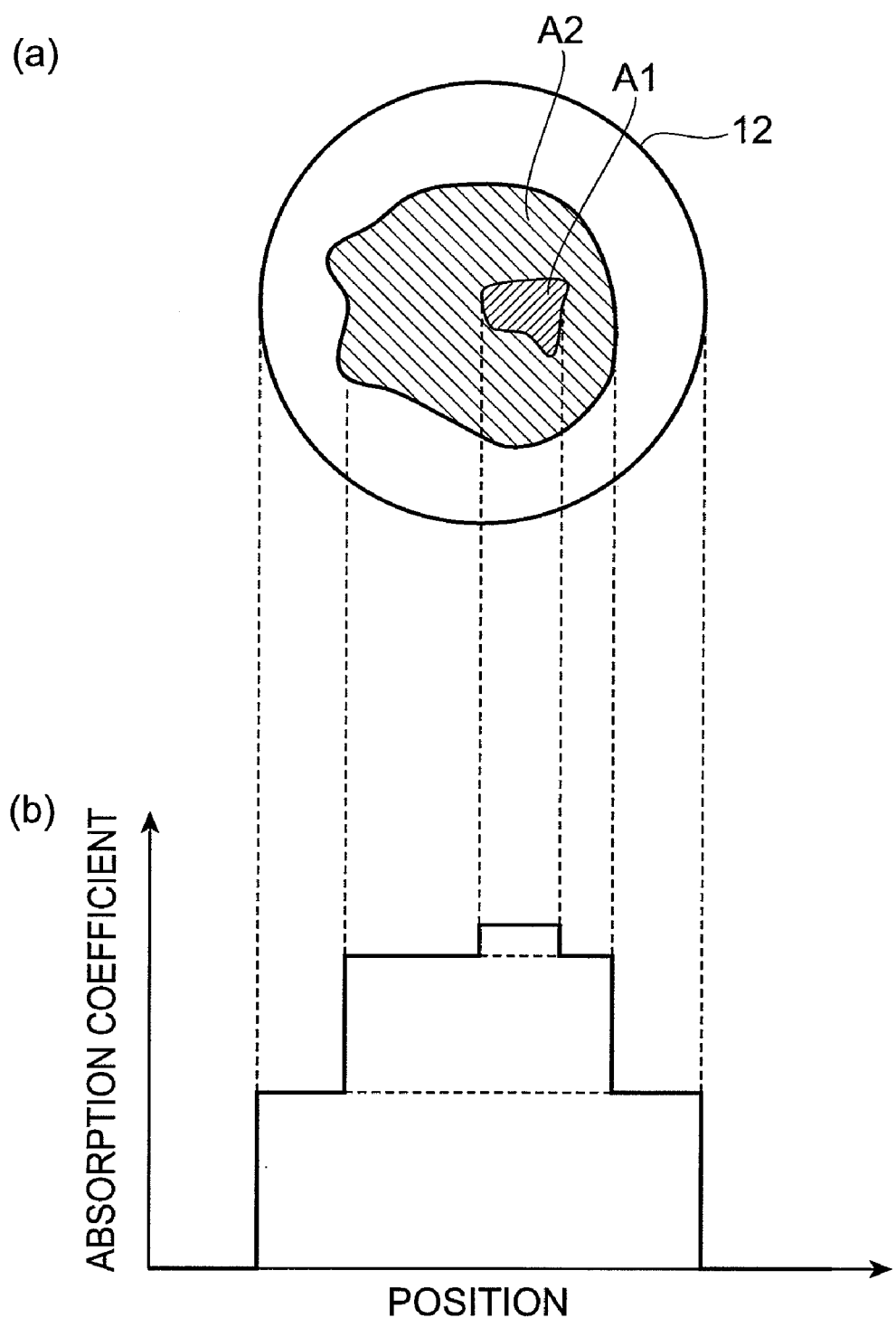
[FIGS. 8A and 8B] are conceptual diagrams of a spatial distribution of absorption coefficient in the interior of the container and show a result of integration of the internal information measurement result and the contour measurement result.

The computing/controlling unit 14 then integrates the computation results shown in FIGS. 6 and 7 to provide image information, etc., indicating a location of the tumor or other absorbing body with respect to the entirety of the measured region B as shown in FIGS. 8A and 8B.

Figure 9:
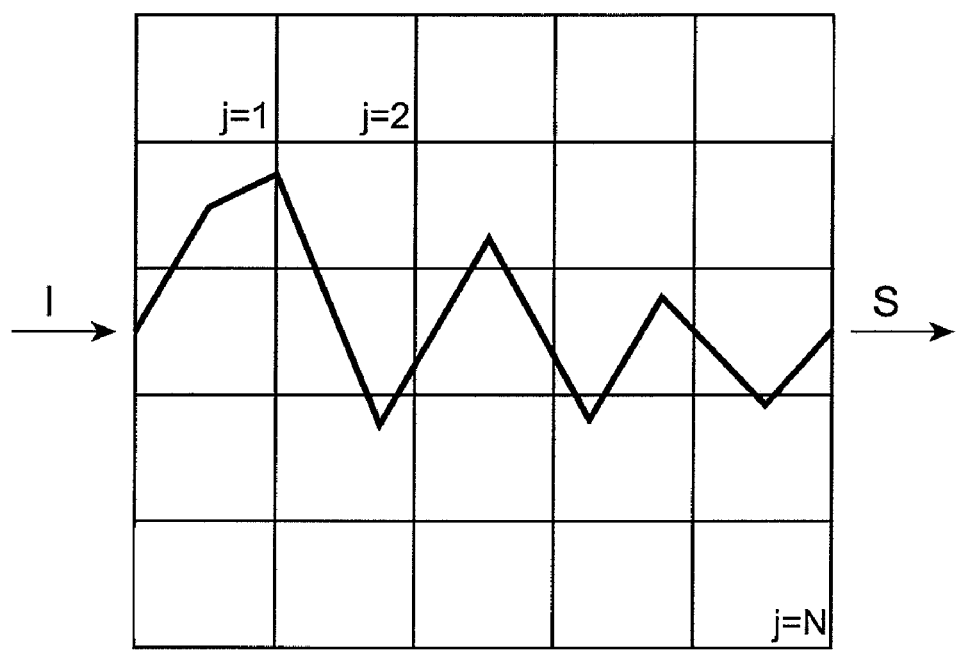
[FIG. 9] is a diagram of a manner in which light is transmitted through a medium that is uniform in absorption coefficient.
Figure 10:
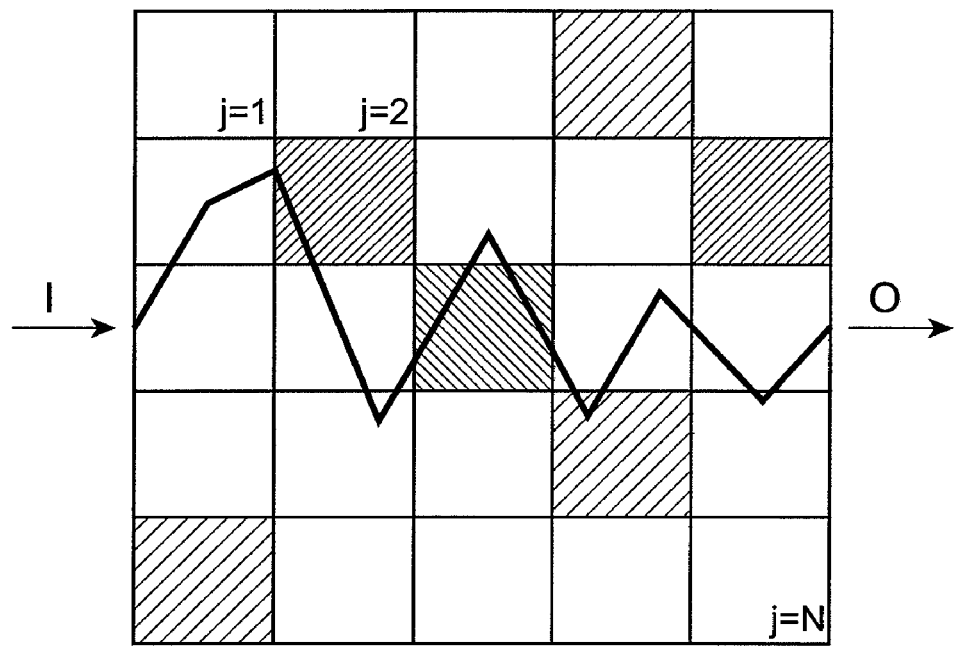
[FIG. 10] is a diagram of a manner in which light is transmitted through a medium that is non-uniform in absorption coefficient.

Basic principles of a method of computing the absorption coefficient distribution by the computing/controlling unit 14 shall now be described. FIG. 9 is a diagram of a manner in which light is transmitted through a medium that is uniform in absorption coefficient. FIG. 10 is a diagram of a manner in which light is transmitted through a medium that is non-uniform in absorption coefficient. To simplify the description, a medium that is a scattering/absorbing body shall be considered to have a square shape that spreads two-dimensionally, and this medium is divided into N (=25) square volume elements (area elements to be more precise because the elements are two-dimensional) of equal size. It shall be considered that inside each individual volume element, the absorption coefficient is fixed and that a volume element indicated with slanted line portions, etc., differs in absorption coefficient in comparison to other volume elements.

In a case where light is projected into the interior of the medium that is uniform in absorption coefficient (absorption coefficient: $\mu_a$) from one point of the medium and output light is detected from one point as shown in FIG. 9, a detected light amount S is expressed as follows using an incident light amount I, degrees of influence $W_j$ (j=1 to N) of the respective volume elements, and a decay constant $D_{sr}$ indicating a proportion of the incident light that is emitted to the exterior of the medium by scattering, reflection, etc.:

[Formula 1]

$$S = D_{sr} \cdot I \cdot \exp\{-\mu_a(W_1 + W_2 \ldots + W_N)\} \tag{1}$$

Here, the degrees of influence of the respective volume elements refer to proportions of change of the detected light amount that accompany changes of the absorption coefficients of the respective volume elements in the case of projecting light from a single point and detecting light at a single point, and a specific computation method shall be described below.

Next, the absorption coefficients of the respective volume elements of the medium having different absorption coefficients $\mu_{aj}$ (j=1 to N) according to the volume elements as shown in FIG. 10 are expressed as follows using a reference absorption coefficient $\mu_a$ and changes $\Delta\mu_{aj}$ (j=1 to N) with respect to $\mu_a$ of the absorption coefficients of the respective volume elements:

[Formula 2]

$$\mu_{aj} = \mu_a + \Delta\mu_{aj} \ (j+1, 2, \ldots N) \tag{2}$$

and if the decay constant $D_{sr}$ does not differ from the case where the absorption coefficient is uniform, a detected light amount O in this case is expressed as follows:

[Formula 3]

$$O = D_{sr} \cdot I \cdot \exp\{-[W_1(\mu_a + \Delta\mu_{a1}) + W_2(\mu_a + \Delta\mu_{a2}) + \ldots + W_N(\mu_a + \Delta\mu_{aN})]\} \quad (3)$$
$$= S \cdot \exp\{-[W_1\Delta\mu_{a1} + W_2\Delta\mu_{a2} + \ldots + W_N\Delta\mu_{aN}]\}$$

Thus by determining logarithms of both sides of Formula (3), the following formula is derived:

[Formula 4]

$$\ln S - \ln O = (W_1\Delta\mu_{a1} + W_2\Delta\mu_{a2} + \ldots + W_N\Delta\mu_{aN}) \quad (4)$$
$$= \sum_{j=1}^{N} W_j \Delta\mu_{aj}$$

Here, Formula (4) is a function of the detected light amount S (hereinafter referred to as the "reference light amount S") of the light projected from one point and output from one point of the medium that is uniform in absorption coefficient, the detected light amount O (hereinafter referred to as the "measured light amount O") of the light projected from one point and output from one point of the medium that is not uniform in absorption coefficient, the degrees of influence $W_j$ (j=1 to N) in the respective volume elements, and the changes $\Delta\mu_{aj}$ (j=1 to N) with respect to $\mu_a$ of the absorption coefficients of the respective volume elements. Of the above variables, the reference light amount S and the measured light amount O are acquired by measurement, the degrees of influence $W_j$ (j=1 to N) of the respective volume elements are acquired by calculation (details shall be described below), and thus only the N changes $\Delta\mu_{aj}$ (j=1 to N) from $\mu_a$ of the absorption coefficients of the respective volume elements are the unknowns. Thus, by setting up N simultaneous equations shown in Formula (4) for sets of different light projection points and light detection points, the N of $\Delta\mu_{aj}$ can be determined and the spatial distribution of the absorption coefficient of the medium can be calculated.

Specifically, if $S_i$ is the reference light amount, $O_i$ is the detected light amount, and $W_{ij}$ (j=1 to N) are the degrees of influence of the respective volume elements for an i-th (i=1 to N) set of the light projection point and light detection point, Formula (4) is expressed as Formula (5):

[Formula 5]

$$\ln S_i - \ln O_i = \sum_{j=1}^{N} W_{ij}\Delta\mu_{aj} \quad (5)$$

Formula (5) for all of i can be arranged and expressed in matrix form as follows:

[Formula 6]

$$\begin{pmatrix} \ln S_1 - \ln O_1 \\ \ln S_2 - \ln O_2 \\ \vdots \\ \ln S_N - \ln O_N \end{pmatrix} = \begin{pmatrix} W_{11} & W_{12} & \cdots & W_{1N} \\ W_{21} & W_{22} & & \vdots \\ \vdots & & \ddots & \vdots \\ W_{N1} & \cdots & \cdots & W_{NN} \end{pmatrix} \begin{pmatrix} \Delta\mu_{a1} \\ \Delta\mu_{a2} \\ \vdots \\ \Delta\mu_{aN} \end{pmatrix} \quad (6)$$

The N of $\Delta\mu_{aj}$, that is, the spatial distribution of the absorption coefficient of the medium can thus be determined as shown in Formula (7):

[Formula 7]

$$\begin{pmatrix} \Delta\mu_{a1} \\ \Delta\mu_{a2} \\ \vdots \\ \Delta\mu_{aN} \end{pmatrix} = \begin{pmatrix} W_{11} & W_{12} & \cdots & W_{1N} \\ W_{21} & W_{22} & & \vdots \\ \vdots & & \ddots & \vdots \\ W_{N1} & \cdots & \cdots & W_{NN} \end{pmatrix}^{-1} \begin{pmatrix} \ln S_1 - \ln O_1 \\ \ln S_2 - \ln O_2 \\ \vdots \\ \ln S_N - \ln O_N \end{pmatrix} \quad (7)$$

A method for determining the degrees of influence $W_{ij}$ (j=1 to N) of the respective volume elements shall now be described. A steady state light diffusion equation for continuous light (luminous flux) that is made incident on each volume element is expressed as follows:

[Formula 8]

$$\Delta\Phi - \mu_a D^{-1}\Phi = O \quad (8)$$

In the above, $\Phi$: luminous flux (light density per unit volume)
$\mu_a$: light absorption coefficient of each volume element
$\mu'_s$: isotropic light scattering coefficient of each volume element
D: diffusion coefficient of each volume element $$D = \frac{1}{3\mu'_s}$$

A boundary condition between the interior and the exterior of the medium is given by:
[Formula 9]

$$\Phi_{BL} = 0 \quad (9)$$

The subscript BL expresses the boundary between the interior and the exterior of the medium. Formula (9) is equivalent to a condition in which light is completely absorbed at the boundary, that is, for example, a state where the surroundings of the medium is colored completely black.

For each set of the light projection point and light detection point, that is, for each i-th (i=1 to N) set of the light projection point and light detection point, Formulae (8) and (9) are used to perform a light transmission simulation (hereinafter referred to as the "first simulation") and thereby calculate the detected light intensity. Here, in the first simulation, the medium is assumed to have the fixed absorption coefficient $\mu_a$, and further, complete diffusion is assumed in Formula (8) above and the size of the container 12 is assumed to be greater than $1/\mu'_s$. $d_{i0}$ shall be the detected light amount acquired by the first simulation for the i-th (i=1 to N) set of the light projection point and light detection point.

A second simulation is then performed using Formulae (8) and (9). In the second simulation, a light transmission simulation is performed for each set of the light projection point and light detection point under the assumption that one of the volume elements of the medium has an absorption coefficient $\mu_a + \Delta\mu_a$ that differs from the absorption coefficient $\mu_a$. For example, the detected light intensity is calculated by letting $\Delta\mu_a = 0.01$[mm$^{-1}$]. $d_{ij}$ shall be the detected light amount for the i-th (i=1 to N) set of the light projection point and light detection point in the case where the absorption coefficient of the j-th (j=1 to N) volume element is changed.

The degrees of influence $W_{ij}$ of the respective volume elements are expressed as follows by Formula (10) using the detected light amounts calculated by the first simulation and the second simulation:

[Formula 10]

$$W_{ij} = \mu_a^{-1} \ln(d_{io}/d_{ij}) \tag{10}$$

$W_{ij}$ are thus determined from Formula (10), and consequently, the spatial distribution of the absorption coefficient is calculated from Formula (7).

Although a case where the number of equations shown in Formula (4) is equal to the number of volume elements was described, even in a case where the number of equations is less than the number of volume elements or greater than the number of volume elements, a singular problem can be converted to a non-singular problem by using a singular value decomposition method, etc., and the spatial distribution of the absorption coefficient can thus be determined.

Effects exhibited by the bioinstrumentation apparatus 10 according to the present embodiment shall now be described. As described above, with the bioinstrumentation apparatus 10, internal information measurement and contour measurement can be performed. In the internal information measurement, the light (first light) of the wavelength λ1 at which the absorption coefficient μab of the measured region B and the absorption coefficient μai of the optical interface material 20 are practically equal is used to measure the spatial distribution of the absorption coefficient in the interior of the container 12. Thus, in the internal information measurement, reflection, scattering, etc., of light at the surface of the measured region B is prevented to enable the position and size of a tumor or other light absorbing body on the basis of the light irradiation positions and detection positions to be measured with good precision. Meanwhile, in the contour measurement, the light (second light) of the wavelength λ2 at which the absorption coefficient μab of the measured region B is greater than the absorption coefficient μai of the optical interface material 20 is used to measure the spatial distribution of the absorption coefficient in the interior of the container 12. Thus, in the contour measurement, the contour of the measured region B on the basis of the light irradiation positions and detection positions can be measured with good precision. By then integrating the result of the internal information measurement and the result of the contour measurement, the location of the light absorbing body with respect to the entirety of the measured region B can be measured.

Thus, with the bioinstrumentation apparatus 10 of the present embodiment, not only the presence/non-presence and size of a tumor or other light absorbing body but the location of the light absorbing body with respect to the entirety of the measured region B can be measured with good precision in the apparatus that irradiates light onto the measured region B of the subject and detects the diffused light to acquire the internal information on the measured region B.

Also as shown in FIG. 5, it is even better for the absorption coefficient μai(λ1) of the optical interface material 20 with respect to the light (first light) of the wavelength λ1 to be greater than the absorption coefficient μai(λ2) of the optical interface material 20 with respect to the light (second light) of the wavelength λ2. In the case where the absorption coefficient μab(λ1) of the measured region B at the wavelength λ1 and the absorption coefficient μab(λ2) of the measured region B at the wavelength λ2 are equal to each other (in the case of graph curve G3 shown in FIG. 5) or in the case where the absorption coefficient μab(λ1) of the measured region B is less than μab(λ2) (in the case of graph curve G4 shown in FIG. 5), the relationships where the absorption coefficients μab(λ1) and μai(λ1) of the measured region B and the optical interface material 20 are practically equal at the wavelength λ1 and the absorption coefficient μab(λ2) of the measured region B is greater than the absorption coefficient μai(λ2) of the optical interface material 20 at the wavelength λ2 can be realized favorably by setting the absorption coefficient μai of the optical interface material 20 as described above. Or, even in the case where the absorption coefficient μab(λ1) of the measured region B is greater than μab(λ2) (in the case of graph curve G2 shown in FIG. 5), by adjusting the light absorbing characteristics of the optical interface material 20 and setting the wavelengths λ1 and λ2 so that a difference of the absorption coefficients of the optical interface material 20 (μai(λ1)−μai(λ2)) is greater than a difference of the absorption coefficients of the measured region B (μab(λ1)−μab(λ2)), the above relationships can be realized favorably. The internal information measurement and the contour measurement can thus be performed favorably.

MODIFICATION EXAMPLE

Figure 11:
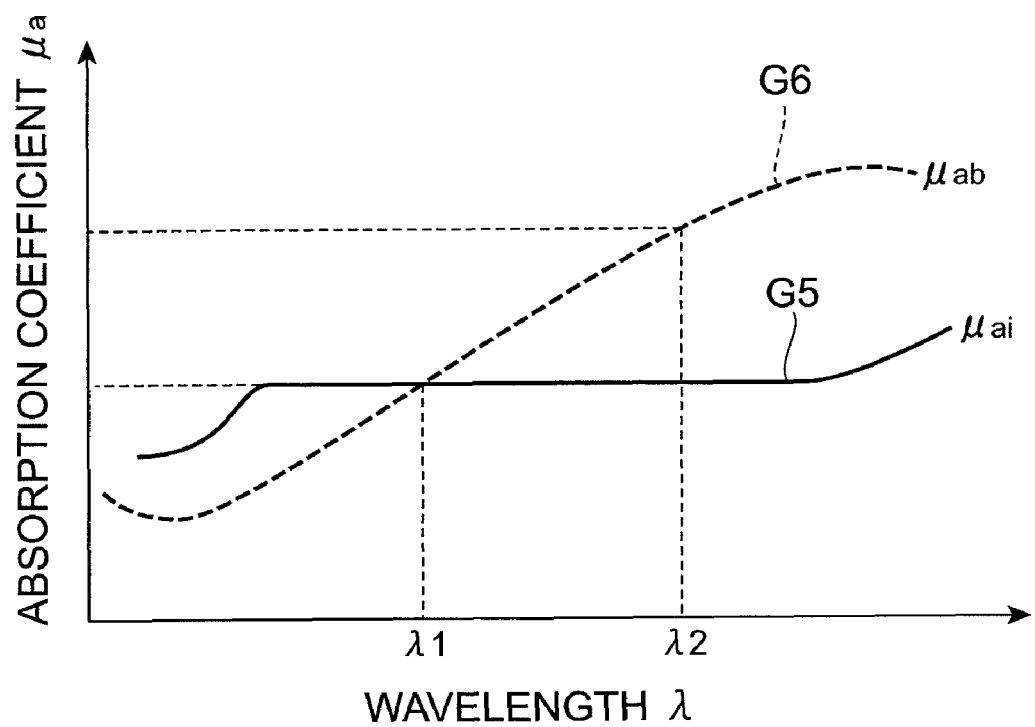
[FIG. 11] is a graph of another example of a relationship of absorption coefficients of an optical interface material and a measured region and a wavelength of light as a modification example.

FIG. 11 is a graph for describing a modification example of the above-described embodiment and shows another example of the relationship of the absorption coefficients μai and μab of the optical interface material 20 and the measured region B and the wavelengths λ1 and λ2. In FIG. 11, graph curve G5, indicated by a solid line, indicates an example of a relationship between the absorption coefficient μai of the optical interface material 20 and the wavelength of light (a case where the absorption coefficient μai of the optical interface material 20 hardly changes with increase or decrease of wavelength). Graph curve G6, indicated by a broken line, indicates an example of a relationship between the mean value μab of the absorption coefficient of the measured region B and the wavelength of light (a case where the absorption coefficient μab of measured region B increases with an increase of wavelength).

Even in the case where the optical interface material 20 and the measured region B have the light absorbing characteristics such as shown in FIG. 11, the wavelength λ1 of the first light is set to a wavelength at which the mean value μab of the absorption coefficient of the measured region B and the absorption coefficient μai of the optical interface material 20 are substantially equal (that is, μab(λ1)=μai(λ1)). Also, the wavelength λ2 of the second light is set to a wavelength at which the mean value μab of the absorption coefficient of the measured region B is greater than the absorption coefficient μai of the optical interface material 20 (that is, μab(λ2)>μai(λ2)). That is, the wavelength λ2 is set to a longer wavelength than the wavelength λ1.

In such a case where the absorption coefficient μab(λ1) of the measured region B is less than μab(λ2) (that is, μab(λ1)<μab(λ2)), the absorption coefficients μai(λ1) and μai(λ2) of the optical interface material 20 may be set to be practically equal. The relationships where the absorption coefficients μab(λ1) and μai(λ1) of the measured region B and the optical interface material 20 are practically equal at the wavelength λ1, and the absorption coefficient μab(λ2) of the measured region B is greater than the absorption coefficient μai(λ2) of the optical interface material 20 at the wavelength λ2 can thereby be realized favorably. The internal information measurement and the contour measurement can thus be performed favorably.

The bioinstrumentation apparatus according to the present invention is not restricted to the embodiment and modification example described above and various other modifications are possible. For example, although with the embodiment described above, a laser diode was indicated as an example of the light source, a solid-state laser, a dye laser, or a gas laser may be used as the light source. Or, light resulting from wavelength selection of light from an LED or a white light source by a wavelength selector may be used.

Also, although with the embodiment described above, an analysis method in a case of using continuous light as the irradiated light was described, the present invention is also applicable to a bioinstrumentation apparatus that adopts time resolved spectroscopy (TRS) with which internal information of a measured region is acquired from a time resolved waveform of diffused light acquired by using pulsed light as well as to a bioinstrumentation apparatus that adopts phase modulation spectroscopy (PMS) with which internal information of a measured region is acquired from light intensity and phase information of diffused light acquired using phase modulated light.

Also, although with the embodiment described above, a breast was indicated as an example of the measured region, the bioinstrumentation apparatus according to the present invention is also applicable to measuring a head, hand, foot, trunk, or other living object region.

Also, the medium (optical interface material) filling the interior of the container is not restricted to a liquid medium and, for example, a liquid or gel material that solidifies with the elapse of time may be used. By using a medium made of a material that solidifies with time, the measured region can be fixed to improve the measurement precision, and the burden of the subject can be reduced because the measurement can be made at a comfortable posture.

The invention claimed is:

1. A bioinstrumentation apparatus irradiating light onto a measured region of a subject, detecting diffused light to acquire internal information on the measured region, and comprising:

a container holding a light transmitting medium;

a light irradiation unit including a plurality of light emitting ends fixed to the container and irradiating a first light and a second light that mutually differ in wavelength onto the measured region that is immersed in the medium;

a light detection unit including a plurality of light detecting ends fixed to the container and detecting the diffused light from the measured region; and a computing unit computing the internal information based on an output signal from the light detection unit; and wherein the wavelength of the first light is a wavelength at which a mean value of absorption coefficient of the measured region and absorption coefficient of the medium are substantially equal, the wavelength of the second light is a wavelength at which the mean value of the absorption coefficient of the measured region is greater than the absorption coefficient of the medium, and the computing unit computes the internal information based on an output signal related to diffused light of the first light and computes boundary information between the measured region and the medium based on an output signal related to diffused light of the second light.

2. The bioinstrumentation apparatus according to claim 1 wherein the absorption coefficient of the medium with respect to the first light is greater than the absorption coefficient of the medium with respect to the second light.

3. The bioinstrumentation apparatus according to claim 1 wherein the absorption coefficient of the medium with respect to the first light is practically equal to the absorption coefficient of the medium with respect to the second light.

4. The bioinstrumentation apparatus according to claim 1 wherein the computing unit integrates the internal information and the boundary information.

* * * * *